(12) United States Patent
Steinemann et al.

(10) Patent No.: US 6,702,855 B1
(45) Date of Patent: Mar. 9, 2004

(54) OSTEOPHILIC IMPLANTS

(75) Inventors: Samuel G. Steinemann, Sulpice (CH); James Simpson, Eptingen (CH)

(73) Assignee: Institut Straumann AG (CH)

( * ) Notice: Subject to any disclaimer, the term of this patent is extended or adjusted under 35 U.S.C. 154(b) by 0 days.

(21) Appl. No.: 09/890,087

(22) PCT Filed: Jan. 27, 2000

(86) PCT No.: PCT/EP00/00619
§ 371 (c)(1),
(2), (4) Date: Oct. 1, 2001

(87) PCT Pub. No.: WO00/44305
PCT Pub. Date: Aug. 3, 2000

(30) Foreign Application Priority Data

Jan. 29, 1999 (EP) .............................. 99810078

(51) Int. Cl.$^7$ ................................... A61F 2/28
(52) U.S. Cl. .................................... 623/23.53
(58) Field of Search ......................... 623/16.11, 18.11, 623/23.15, 23.5, 23.53, 23.55, 11.11

(56) References Cited

U.S. PATENT DOCUMENTS

| | | | | |
|---|---|---|---|---|
| 3,707,006 A | * | 12/1972 | Bokros et al. | 424/422 |
| 3,855,638 A | * | 12/1974 | Pillar | 623/23.55 |
| 5,034,186 A | * | 7/1991 | Shimamune et al. | 419/9 |
| 5,674,290 A | * | 10/1997 | Li | 424/423 |
| 5,800,542 A | * | 9/1998 | Li | 424/423 |
| 6,491,723 B1 | * | 12/2002 | Beaty | 623/11.11 |

FOREIGN PATENT DOCUMENTS

| | | |
|---|---|---|
| EP | 0 388 575 A1 | 3/1989 |
| EP | 0 606 566 A1 | 7/1994 |

* cited by examiner

*Primary Examiner*—Kevin Shaver
*Assistant Examiner*—Michael B. Priddy
(74) *Attorney, Agent, or Firm*—McCarter & English, LLP

(57) ABSTRACT

The invention relates to an osteophilic implant having improved osteointegration characteristics. The implant consists of titanium or a titanium alloy and is suitable for the implantation in bones. The implant is provided with a rouge, hydroxylated and hydrophilic surface which is at least sealed in a gastight and liquidtight covering. The interior of said covering is provided with an inert atmosphere, preferably consisting of nitrogen, oxygen and/or inert gas and/or is at least partially filled with purified water which optionally contains additives. The invention also relates to a method for producing the same.

41 Claims, No Drawings

OSTEOPHILIC IMPLANTS

The present invention relates to osteophilic implants which can be inserted into bones and which have considerably improved osteointegration characteristics, and to processes for their production.

Implants which can be inserted into bones, for example artificial hip or knee joints or pins to be screwed into the jaw for constructing artificial teeth, are known per se.

Such implants preferably consist of titanium or titanium-based alloys, e.g. titanium/zirconium alloys, which can also contain niobium, tantalum or other tissue-compatible metal additives. A key characteristic of such implants is their osteo-integration time, i.e. the time taken by the bony substance to bond, or integrate, permanently and sufficiently strongly with the implant surface.

How strongly the implant is anchored in the bone can be determined by mechanical measurements, namely by measuring the force (as traction, pressure, shear or torque) which are necessary to pull or twist the implant anchored in the bone out of its anchorage, i.e. to break the adhesion between the surface of the implant and the bony substance bonded thereto. Such methods of measurement are known per se and are described for example in Brunski, Clinical Materials, vol. 10, 1992, pp. 153–201. Measurements have shown that titanium implants with a smooth surface structure do not anchor satisfactorily in the bone, whereas implants with a roughened surface produce a notable improvement in the bone-implant bond in terms of the tensile strength.

EP 0 388 575 therefore proposes firstly to create a macro-roughness on the implant surface by sandblasting and then to cover this with a micro-roughness by treatment in an acid bath. Thus the implant surface can be roughened by sandblasting and then treated with an etching reagent, e.g. hydrofluoric acid or a hydrochloric acid/sulfuiric acid mixture. The surface thus provided with a defined roughness is then washed with water and solvents and subjected to a sterilization treatment.

EP 0 606 566 proposes to treat the implant surface under vacuum firstly with an inert plasma gas, in order to clean the surface, and then with an oxidizing plasma gas or by thermal oxidation and with any other relevant process steps, after which the implant is sealed in glass ampoules and sterilized. All these steps are preferably carried out under vacuum. Said process causes a surface oxide to grow.

Although clean, this surface is immediately contaminated or extensively chemically inactivated in the air.

The chemical state of the surface of titanium and titanium-based alloys is complex. It is assumed that the surface of titanium metal oxidizes spontaneously in air and water and that a reaction then takes place with water on the surface, i.e. in the outermost atomic layer, to form hydroxyl groups. This surface containing hydroxyl groups is referred to in the literature as a "hydroxylated" surface; cf. H. P. Boehm, Acidic and Basic Properties of Hydroxylated Metal Oxide Surfaces, Discussions Faraday Society, vol. 52, 1971, pp. 264–275. A metal surface whose hydroxyl groups are not freely available, e.g. because of chemical modification, is not a "hydroxylated" surface in terms of the present invention.

In terms of the present invention, the metal implant surface is referred to as "hydrophilic" if it is freely accessible to the body fluid and not covered with foreign substances, for example substances with a hydrophobic action. Thus various readily volatile hydrocarbons are conventionally present in non-purified air. These are rapidly adsorbed in a thin layer by hydroxylated and hydrophilic titanium metal surfaces, whereby such surfaces are no longer hydrophilic. Likewise, such a hydroxylated and hydrophilic surface can become hydrophobic if the hydroxyl groups present on the surface associate or react chemically e.g. with carbon dioxide present in the air or with organic solvents, such as methanol or acetone, introduced via the cleaning process.

It has now been found that a hydroxylated and hydrophilic surface of titanium or a titanium alloy has biological properties or is biologically active. This surface can also be referred to as pseudo-biologically active. The expression "biologically active" will be used hereafter. It has been found, surprisingly, that such a biologically active surface, e.g. in the form of an implant, knits with the bony substance to form a strong bond considerably faster than an equivalent surface which is not hydroxylated and/or not hydrophilic. It has further been found that the biological activity of such a metal surface is very quickly lost in the presence of carbon dioxide or volatile hydrocarbons, i.e. in contact with normal air, for example in the drying process, or on cleaning with alcohol. It has also been found that the biological activity of said hydroxylated and hydrophilic surface can be maintained extensively unchanged if this surface is treated according to the present invention, as described below. In this way the biological activity of the implant surface is maintained up to the point of implantation.

The present invention is defined in the Claims. The present invention relates in particular to an osteophilic implant with improved osteointegration characteristics or with improved osteointegration, said implant consisting of titanium or a titanium alloy and being suitable for implantation in bones, characterized in that the implant has a roughened, hydroxylated and hydrophilic surface and hence a biologically active surface.

This surface is preferably sealed in a gas-tight and liquid-tight covering, the interior of the covering being devoid of any compounds capable of impairing the biological activity of the implant surface.

Preferably, the interior of the covering is at least partially filled with pure water optionally containing additives, the amount of water present being at least sufficient to ensure moisturization or wetting of the roughened implant surface. The remaining volume inside the covering can be filled with gases inert towards the implant surface, e.g. oxygen, nitrogen, noble gases or a mixture of such gases.

The present invention further relates to a process for the production of the implants according to the invention.

The implants according to the invention preferably consist of a titanium alloy, particularly preferably a titanium/zirconium alloy, which can also contain niobium, tantalum or other tissue-compatible metal additives. These implants are preferably used as artificial hip or knee joints or as pins to be screwed into the jaw for constructing artificial teeth. Such implants, their nature and the metal materials used to produce them are known per se and are described for example in J. Black, G. Hastings, Handbook of Biomaterials Properties, pages 135–200, published by Chapman & Hall, London, 1998.

The structural and functional anchorage of e.g. a dental implant in the bone is normally achieved by applying a macro-roughness, such as a screw thread or depressions in the surface, and/or optionally a micro-roughness as well, the micro-roughness being applied either in an additive process by plasma technology or in a subtractive process by chemical etching on the surface. How strongly the implant is anchored in the bone can be determined by mechanical measurements, as already described at the outset in this text.

Numerous studies have shown that adequate anchorage of an implant in the bone depends to a large degree on the nature of the implant surface, especially the roughness. It is notable that the use of a biologically active implant surface according to the present invention is extensively independent of the physical nature of the implant surface. According to the present invention the biological action of the hydroxylated and hydrophilic surface is added synergistically to the substantially physical action of the surface roughness, resulting in a considerable improvement in the osteointegration. According to the present invention, the two effects are interlinked inasmuch as a physically larger surface also increases the availability of biologically active surface. The present invention shows that the osteointegration is decisively influenced not only by the surface roughness per se but also by the chemical nature of the surface.

Analyses by XPS (X-ray excited photoelectron spectroscopy) and Auger electron spectroscopy (AES) of implant surfaces used for clinical purposes (prior to implantation) indicated that the surface was contaminated with carbon. Wetting experiments showed a wetting angle with water of 70° or more ($\geq 70°$), i.e. a water-repellent surface of hydrophobic character. Other studies showed that such surfaces are biologically inactive. Surprisingly, it was found that the hydroxylated and hydrophilic surface, e.g. as obtained directly after acid etching, has a wetting angle with water of less than 50° (<50°) when the water drop in contact with the surface is advancing, or of less than 20° (<20°) when the drop is receding, and has a notable biological activity, said activity being substantially maintained if further cleaning and sterilization processes are dispensed with and contact of the implant surface with the air is avoided.

The present invention is based on the biological action, in terms of osteointegration, of implants made of titanium or titanium alloys, said implants having a hydroxylated and hydrophilic surface and at the same time—on account of its roughness—an enlarged active surface. This biologically active surface can be prepared e.g. by machining and structuring, shot peening, sandblasting and subsequent chemical treatment, e.g. etching with acid, or by using an electrochemical (electrolytic) treatment, or by a combination of such processes.

The surface according to the invention can be prepared for example by providing the surface with the desired roughness or texture and keeping the surface in the resulting state if it is already hydroxylated and hydrophilic, or converting the roughened and treated surface to a hydroxylated and hydrophilic state in a separate process step. In particular, the implant can be produced by shot peening or sandblasting the implant surface and/or roughening it by using plasma technology, and then treating the mechanically roughened surface by an electrolytic or chemical process until a hydroxylated and hydrophilic surface is formed. The implant is preferably etched with an inorganic acid or a mixture of inorganic acids, particularly preferably with hydrofluoric acid, hydrochloric acid, sulfuric acid, nitric acid or a mixture of such acids, or the surface is activated with hydrochloric acid, hydrogen peroxide and water in a weight ratio of about 1:1:5. The surface is then washed with pure water in an inert atmosphere. The preferred procedure is to shot-peen the implant and then etch it with dilute hydrofluoric acid at room temperature; or sandblast the implant, e.g. with aluminium oxide particles having a mean size of 0.1–0.25 mm or 0.25–0.5 mm, and then treat it at elevated temperature with a hydrochloric acid/sulfuric acid mixture and wash it with pure distilled and $CO_2$-free water; or sandblast the implant with coarse particles, e.g. with a mixture of particles as defined above, and then treat it with a hydrochloric acid/nitric acid mixture and wash it with pure distilled and $CO^2$-free water; or treat the implant with a mixture of hydrochloric acid, hydrogen peroxide and water in a weight ratio of about 1:1:5 and wash it with pure distilled and $CO_2$-free water; or roughen the implant by using plasma technology and then hydroxylate it in a mixture of hydrochloric acid, hydrogen peroxide and water in a weight ratio of about 1:1:5 and wash it with pure distilled and $CO_2$-free water; or treat the implant by an electrolytic process, optionally after mechanical roughening of the surface, and then wash it with pure distilled and $CO_2$-free water.

Whatever the case may be, according to the invention the implant is not subjected to further aftertreatment, i.e. it is not treated with alcohol, acetone or any other organic solvent. In particular, said pure water contains neither carbon dioxide nor hydrocarbon vapours and especially no acetone and no alcohols like methanol or ethanol. However, it can contain special additives as described below. The "pure" water used for washing has preferably been distilled several times or prepared by reverse osmosis; the water has preferably been prepared in an inert atmosphere, i.e. under reduced pressure in a nitrogen or noble gas atmosphere, for example.

Furthermore, the pure water has a resistivity of at least 2 Mohm·cm (resistivity>2 Mohm·cm) and a total organic carbon (TOC) content of at most 10 ppb ($\leq 10$ ppb).

Following the washing process, the implant obtained is left in pure water and stored in a closed vessel or a covering. In addition to water, the interior of the covering can contain inert gases, for example nitrogen, oxygen or a noble gas such as argon. The implant obtained is preferably stored in pure water optionally containing selective additives, and in a covering which is practically impermeable to gases and liquids, especially to carbon oxides, the interior of the covering being devoid of any compounds capable of impairing the biological activity of the implant surface.

As already mentioned, examples of compounds capable of impairing the biological activity of the implant surface are methanol, ethanol, acetone and related ketones, and numerous other organic compounds, or carbon dioxide.

In these terms the present invention further relates to a process for the production of an implant according to the invention by shot-peening or sandblasting the implant surface and/or roughening it by using plasma technology, characterized in that (i) the surface roughened mechanically or by plasma technology is then treated by an electrolytic or chemical etching process until a hydroxylated and hydrophilic surface is formed, preferably with an inorganic acid or a mixture of inorganic acids and particularly preferably with hydrofluoric acid, hydrochloric acid, sulfuric acid, nitric acid or a mixture of such acids, or hydrochloric acid, hydrogen peroxide and water in a weight ratio of about 1:1:5;

(ii) the surface is washed in an inert atmosphere with pure water optionally containing additives; and (iii) without carrying out any further treatment, the surface is stored in an inert atmosphere and in the permanent presence of pure water optionally containing additives, preferably in a covering which is practically impermeable to gases and liquids.

The adverse effect of methyl alcohol can be explained e.g. by the fact that methyl alcohol undergoes a condensation reaction with the hydroxyl group located on the surface according to the following formula: $\equiv$TiOH+ $CH_3OH \rightarrow \equiv TiOCH_3 + H_2O$, $\equiv$Ti— being a metal ion on the metal surface. Carbon dioxide, for example, reacts with the hydroxide group to form a bicarbonate complex, which inactivates the hydroxyl group. The reaction of an organic carboxylic acid with the hydroxyl group can be explained analogously. Moreover, an amphoteric character can be ascribed to the surface as a function of the acidity of the electrolyte surrounding the surface, there being an interaction between the acid in the electrolyte and the basic-reacting hydroxyl or between the anion in the electrolyte and the acid-reacting hydroxyl of the oxide. The surface reactions can be explained by the formation of covalent bonds, electrostatic effects and/or the formation of hydrogen bridges. In these terms it is assumed that the hydroxyl groups on the implant surface are the actual carriers of the biological activity and act directly on the bone minerals and the organic bony substance with which they come into contact and react after implantation.

However, the present invention is not tied to these explanations. The decisive point is the fact that certain compounds have an adverse effect on the biological activity of a hydroxylated and hydrophilic surface according to the invention and that they reduce or totally eliminate this activity in respect of the biological body substance. Those skilled in the art can determine by experiment whether and to what extent a compound adversely affects the biological activity, for example as described below, inter alia.

The implant according to the invention, or at least its hydroxylated and hydrophilic surface, is preferably sealed in a gas-tight and liquid-tight covering, the interior of the covering being devoid of any compounds capable of impairing the biological activity of the implant surface. This gas-tight and liquid-tight covering is preferably a heat-sealed ampoule made of glass, metal, a synthetic polymer or some other gas-tight and liquid-tight material, or a combination of these materials. The metal preferably takes the form of a thin sheet, it being possible for polymeric materials and metal sheets, as well as glass, to be combined together to form a suitable packaging in a manner known per se.

Preferably, the interior of the covering is at least partially filled with purified water optionally containing additives, the amount of water present being at least sufficient to ensure moisturization of the implant surface. Surprisingly, it has been found that moisturizing the implant surface according to the invention with pure water stabilizes its chemical and biologically active state and maintains it for a prolonged period, normally up to the point of implantation. It has also been found that the osteointegration characteristics of the surface can be further improved by suitable additives. In these terms, for example, the cell adhesion to the implant surface is improved and the anchoring time of the implant in the bone is shortened. It could also be said that the implant surface has osteophilic (or osseophilic) characteristics which are improved by suitable additives. Examples of suitable additives which can be incorporated according to the invention in the pure water are monovalent alkali metal cations, such as $Na^+$ or $K^+$ or a mixture of $Na^+$ or $K^+$, with appropriate anions in the form of inorganic salts, e.g. sodium chloride, potassium chloride, sodium or potassium chlorate, sodium or potassium nitrate, sodium or potassium phosphate or a mixture of such salts. It is also possible to add divalent cations in the form of water-soluble inorganic salts, suitable cations being particularly $Mg^{2+}$, $Ca^{2+}$, $Sr^{2+}$ and/or $Mn^{2+}$ in the form of the chlorides, or mixtures thereof, and other suitable anions being phosphate and phosphonate anions, which are understood to include monoorthophosphate anions and diorthophosphate anions or monoorthophosphonate anions and diortho-phosphonate anions, in combination with said cations.

Preferred cations and anions are those which already occur in the body fluid, especially at the appropriate physiological concentration and with a physiological acidity (pH) ranging preferably from 4 to 9 and particularly preferably from 6 to 8. Preferred cations are $Na^+$, $K^+$, $Mg^{2+}$ and $Ca^{2+}$. The preferred anion is $Cl^-$. The total amount of said cations or anions ranges preferably from about 50 meq/l to 250 meq/l, particularly preferably from about 100 meq/l to 200 meq/l, and is preferably about 150 meq/l, eq/l being the (formula) equivalent weight or corresponding to the atomic weight of the formula unit divided by the valency. meq/l is the milli-equivalent weight per liter. If the covering contains divalent cations, especially $Mg^{2+}$, $Ca^{2+}$, $Sr^{2+}$ and/or $Mn^{2+}$, on their own or in combination with the above-mentioned monovalent cations, the total amount of divalent cations present preferably ranges from 1 meq/l to 20 meq/l.

The coating of the implant surface with water, according to the invention, has the further advantage that when it is removed from the covering, the hydroxylated and hydrophilic implant surface is temporarily protected from the effect of harmful air-borne substances by the aqueous coating of the surface with water optionally containing selected cations and anions.

Methods of measuring metal surfaces—in the present case the effective area of the roughened implant surface provided with a surface texture—are known per se, for example the electrochemical methods of measurement described in detail in P. W. Atkins, Physical Chemistry, Oxford University Press, 1994. The surface can be determined (a) by measuring the electrophoretic mobility, (b) by measuring the surface charge by means of acid-base titration, (c) by means of impedance spectrometry, or (d) by means of voltammetry. Roughness measurements can also be used to obtain the effective surface area as the square of the hybrid parameter $L_r$, i.e. the square of the profile length ratio. DIN 4762 defines the parameter $L_r$, as the ratio of the length of the extended two-dimensional profile to the measured distance. A condition of the latter measurement, however, is that the vertical and lateral resolution is smaller than 1 $\mu$m and even in the order of 0.1 $\mu$m.

The reference surface for all these methods of measurement is the flat polished metal surface. The measured values of the roughened surface compared with those of the flat polished surface indicate by how much the roughened surface is larger than the flat polished surface. In vitro studies with bone cells and in vivo histomorphometric studies on implants according to the invention suggest that the osteophilic characteristics of the implants according to the invention are particularly good when the roughened surface is preferably at least 1.5 times as large and particularly preferably at least twice as large as the comparable flat polished surface. The roughened implant surface is preferably at least 2 to 12 times as large and particularly preferably about 2.5 to 6 times as large as the comparable flat polished surface.

The wetting properties or the hydrophilic character of the implant surface according to the invention can be determined in a manner known per se by measuring the contact angle or wetting angle between the liquid (water) and the dry metal substrate surface by optical methods. For determination of the contact angle of an implant surface according to the invention, the latter is washed with pure water and dried in pure nitrogen or pure argon. One drop of pure water is placed on the horizontally aligned surface. The addition of more water, e.g. with a hollow needle, enlarges the drop surface to give the "upper" contact angle, while the removal of water reduces the drop diameter in contact with the surface to give the "lower" contact angle. The surface is said to have hydrophilic character when the "upper" contact angle is less than 50° (<50°) and the "lower" contact angle is less than 20° (<20°).

Industrially produced surfaces of titanium and titanium alloys for processing in laboratories and clinics normally contain impurities consisting substantially of carbon compounds and traces of nitrogen, calcium, sulfur, phosphorus and silicon. These impurities concentrate in the outermost metal oxide layer. Preferably, the hydroxylated and hydrophilic implant surface contains at most 20 atom % of carbon, measured by spectroscopic methods such as XPS or AES or other spectroscopic methods known per se.

The Examples which follow illustrate the invention.

EXAMPLE 1

A common shape of dental implant in the form of a screw of diameter 4 mm and length 10 mm was produced. The crude shape was obtained in a manner known per se by removing material from the cylindrical blank by turning on a lathe and milling. The surface to be inserted into the bone was then provided with a macro-roughness, in accordance with EP 0 388 575, by being sandblasted with particles having a mean size of 0.25–0.5 mm. The roughened surface (macro-roughness) was then treated for about five minutes at a temperature above 80° C. with an aqueous hydrochloric acid/sulfuric acid mixture having an $HCl:H_2SO_4:H_2O$ ratio of 2:1:1 to give a ratio of the roughened implant surface to the comparable polished surface of 3.6 as measured by voltammetry in an aqueous electrolyte containing 0.15 M NaCl (corresponding to a ratio of 3.9 as measured by impedance spectrometry in a 0.1 molar $Na_2SO_4$ electrolyte). The implant formed in this way was washed with pure water and then a) heat-sealed directly in a glass ampoule filled with pure water, opened after 4 weeks and implanted;

b) heat-sealed directly in a glass ampoule filled with pure water containing 150 meq/l of $Na^+$ ions, 10 meq/l of $Mg^{2+}$ ions and the corresponding amount of $Cl^-$ anions, opened after 4 weeks and implanted; or c) dried with air containing $CO_2$ and implanted (comparative experiment). The implants obtained in experiments a), b) and c) were implanted in the upper jaw of a minipig. The anchorage in the bone was measured as the torque required to loosen the screw implanted in the upper jaw of the minipig. The results obtained are shown in Table 1.

TABLE 1

|  | Anchorage* after 2 weeks (N · cm) | Anchorage* after 3 weeks (N · cm) | Anchorage* after 4 weeks (N · cm) |
|---|---|---|---|
| Experiment a) | 35 | 72 | 100 |
| Experiment b) | 55 | 80 | 110 |
| Comparative experiment c) | 20 | 58 | 80 |

*The anchorage is given as the loosening torque in N · cm (mean values).

The results of experiments a) and b) (implants according to the invention) show that the corresponding loosening torques for the indicated knitting times are markedly greater than those of experiment c).

EXAMPLE 2

Experiments b) and c) of Example 1 were repeated except that the implant was produced with a ratio of the roughened implant surface to the comparable polished surface of 1.9 (measured by impedance spectrometry in a 0.1 molar $Na_2SO_4$ electrolyte). This was done by cutting the implant surface only by mechanical means, namely turning on a lathe, and then etching it as indicated in Example 1. The resulting implant was washed with pure water and then a) heat-sealed directly in a glass ampoule filled with pure water containing 150 meq/l of $Na^+$ ions, 10 meq/l of $Mg^{2+}$ ions and the corresponding amount of $Cl^-$ anions, opened after 4 weeks and implanted; or b) dried with air containing $CO_2$ and implanted (comparative experiment).

The implants obtained in experimnents d) and e) were implanted in the upper jaw of a minipig. The anchorage in the bone was measured as the torque required to loosen the screw implanted in the upper jaw of the minipig. The results obtained are shown in Table 2.

TABLE 2

|  | Anchorage* after 2 weeks (N · cm) | Anchorage* after 3 weeks (N · cm) | Anchorage* after 4 weeks (N · cm) |
|---|---|---|---|
| Experiment d) | 10 | 40 | 65 |
| Comparative experiment e) | 5 | 25 | 60 |

*The anchorage is given as the loosening torque in N · cm (mean values).

The results of experiment d) (implant according to the invention) show that the corresponding loosening torques for the indicated knitting times are markedly greater than those of experiment c). If it is assumed that a loosening torque of at least 35 N·cm is considered in dental surgery to be essential for the construction of the superstructure, the implant according to the invention achieves this value after 3 weeks at the most.

What is claimed is:

1. An implant assembly, comprising an implant having a roughened surface which is both hydroxylated and hydrophilic; and a vessel sized and shaped so as to receive said implant, said vessel having an inert atmosphere.

2. The implant assembly of claim 1, wherein said inert atmosphere is selected from the group consisting of nitrogen, oxygen, or a noble gas.

3. In an implant assembly which includes an implant having a roughened surface, the improvement wherein said roughened surface of said implant is hydroxylated and hydrophilic, said roughened surface of said implant being subjected to a medium which preserves the hydroxylated and hydrophilic surface of said implant.

4. An implant assembly, comprising an implant having a hydroxylated and hydrophilic surface; and a vessel sized and shaped so as to receive said implant, said vessel having an interior with a medium which preserves said hydroxylated and hydrophilic surface of said implant.

5. The implant assembly of claim 4, wherein said medium includes water.

6. The implant assembly of claim 9, wherein said medium includes an inert atmosphere.

7. An implant assembly, comprising an implant having a roughened surface which is both hydroxylated and hydrophilic; and a vessel sized and shaped so as to receive said implant, said vessel being at least partially filled with water in an amount sufficient to ensure wetting of said roughened surface of said implant.

8. The implant assembly of claim 7, wherein said vessel has an inert atmosphere.

9. The implant assembly of claim 8, wherein said inert atmosphere is selected from the group consisting of nitrogen, oxygen or a noble gas.

10. The implant assembly of claim 7, wherein said implant comprises titanium.

11. The implant assembly of claim 7, wherein said implant comprises a titanium/zirconium alloy.

12. The implant assembly of claim 11, wherein said implant comprises a titanium/zirconium alloy selected from the group consisting of niobium, tantalum or tissue-compatible metal additives.

13. The implant assembly of claim 7, wherein said vessel is at least partially filled with water containing additives.

14. The implant assembly of claim 13, wherein the water has a resistivity east 2 Mohm/cm and a total organic carbon content of at most 10 ppb.

15. The implant assembly of claim 13, wherein the water contains monovalent alkali metal cations or divalent cations in the form of water-soluble inorganic salts.

16. The implant assembly of claim 15, wherein the water contains $Na^+$ or $K^+$ or a mixture of $Na^+$ and $K^+$ as monovalent alkali metal cations, having anions in the form of inorganic salts.

17. The implant assembly of claim 16, wherein the inorganic salts are selected from the group consisting of sodium chloride, potassium chloride, sodium or potassium chlorate, sodium or potassium nitrate, sodium or potassium phosphate, sodium or potassium phosphate, and mixtures thereof.

18. The implant assembly of claim 13, wherein the water contains metal ions selected from the group consisting of $Mg^{2+}$, $Ca^{2+}$, $Sr^{2+}$, $Mn^{2+}$ and mixtures thereof.

19. The implant assembly of claim 18, wherein the water contains $Mg^{2+}$ or $Ca^{2+}$, as divalent cations in the form of the chlorides.

20. The implant assembly of claim 13, wherein the water contains cations and anions found in the body fluids.

21. The implant assembly of claim 20, wherein the cations and anions are within physiological concentration.

22. The implant assembly of claim 20, wherein the total amount of cations or anions ranges from about 50 meq/l to 250 meq/l.

23. The implant assembly of claim 20 wherein the total amount of cations or anions ranges from about 100 meq/l to 200 meq/l.

24. The implant assembly of claim 20 wherein the total amount of cations or anions is about 150 meq/l.

25. The implant assembly of claim 20, wherein the cations comprise a divalent cation present in the amount of about 1 meq/l to 20 meq/l.

26. The implant assembly of claim 13, wherein the water has an acidity ranging from about 4 to 9.

27. The implant assembly of claim 13, wherein the water has an acidity ranging from about 6 to 8.

28. The implant assembly of claim 7, wherein said roughened surface of said implant is at least 1.5 times as large as a comparable flat polished surface.

29. The implant assembly of claim 28, wherein said roughened surface of said implant is 2–12 times as large as a comparable flat polished surface.

30. The implant assembly of claim 28, wherein said roughened surface of said implant is 2.5 to 6 times as large as a comparable flat polished surface.

31. The implant assembly of claim 7, wherein said roughened surface of said implant comprises an upper contact angle of less than 50° and a lower contact angle less than 20°.

32. The implant assembly of claim 7, wherein said roughened surface of said implant contains at most 20 atom % of carbon.

33. The implant assembly of claim 7, wherein said vessel is a heat-sealed ampoule made of a material selected form the group consisting of a glass, a metal, a synthetic polymer, a gas-tight and liquid-tight material, and a combination of these materials.

34. The implant assembly of claim 33, wherein the metal is a thin sheets.

35. A process for the production of an implant assembly which includes an implant and a vessel sized and shaped so as to receive the implant, said process comprising the steps of:

(a) forming a roughened surface on the implant;

(b) etching the roughened surface of the implant such that the roughened surface becomes hydroxylated and hydrophilic;

(c) providing the vessel with a preservative medium capable of maintaining the hydroxylated and hydrophilic qualities of the roughened surface of the implant; and (d) placing the implant within the vessel which contains the preservative medium.

36. The process of claim 35, wherein step (b) comprises electrolytically etching the roughened surface of the implant such that the roughened surface becomes hydroxylated and hydrophilic.

37. The process of claim 35, wherein step (b) comprises chemically etching the roughened surface of the implant with at least one inorganic acid such that the roughened surface of the implant becomes hydroxylated and hydrophilic.

38. The process of claim 37, wherein the inorganic acid is selected from the group consisting of hydrofluoric acid, hydrochloric acid, sulfuric acid, nitric acid, and mixtures thereof.

39. The process of claim 38, wherein the inorganic acid is a mixture of hydrochloric acid, hydrogen peroxide and water, and wherein the weight ratio of hydrochloric acid, hydrogen peroxide and water is about 1:1:5.

40. The process of claim 35, wherein the medium includes water.

41. The process of claim 35, wherein the medium includes an inert atmosphere.

* * * * *